United States Patent
Selman et al.

(10) Patent No.: US 11,027,155 B2
(45) Date of Patent: Jun. 8, 2021

(54) METHOD FOR PREVENTION AND TREATMENT OF DIABETIC KIDNEY DISEASE

(71) Applicants: Guillermo Selman, Guilderland, NY (US); Loay Hatem Salman, Selkirk, NY (US)

(72) Inventors: Guillermo Selman, Guilderland, NY (US); Loay Hatem Salman, Selkirk, NY (US)

( * ) Notice: Subject to any disclaimer, the term of this patent is extended or adjusted under 35 U.S.C. 154(b) by 68 days.

(21) Appl. No.: 16/653,665

(22) Filed: Oct. 15, 2019

(65) Prior Publication Data

US 2021/0106557 A1   Apr. 15, 2021

(51) Int. Cl.
| | | |
|---|---|---|
| *A61K 31/353* | (2006.01) | |
| *A61P 13/12* | (2006.01) | |
| *A61K 45/06* | (2006.01) | |

(52) U.S. Cl.
CPC ............ *A61P 13/12* (2018.01); *A61K 31/353* (2013.01); *A61K 45/06* (2013.01)

(58) Field of Classification Search
CPC ........ A61K 45/06; A61K 31/353; A61P 13/12
USPC .......................................................... 514/457
See application file for complete search history.

(56) References Cited

PUBLICATIONS

Nagy et al. J. Biol. Chem, 2019, vol. 294(19), pp. 7864-7877.*

* cited by examiner

*Primary Examiner* — Kahsay Habte (57) ABSTRACT

A method for delaying the progression or preventing Diabetic Kidney Disease by administering to a subject in need a composition containing a therapeutically effective amount of a hyaluronan synthesis inhibitor such as 4-Methylumbelliferone.

2 Claims, 7 Drawing Sheets

|  |  | Control | 4-MU |
|---|---|---|---|
| Kidney | Glomerular injury index | 2.1 (25 to 50 % of glomerular tuft area affected) | 1.2 (less than 25% of glomerular tuft area affected) |
|  | Nodules in mesangial expansion | 26.6% (13.3 out of 50 glomeruli) | 20.4% (10.2 out of 50 glomeruli) |
|  | Nodular glomerulosclerosis | 13.4% (6.7 out of 50 glomeruli) | 6% (3 out of 50 glomeruli) |
|  | Nephritis and tubulitis | 33% (2 out of 6 animals) | not observed (0 out of 5 animals) |
|  | Fibrosis | less than 20% | less than 20% |

METHOD FOR PREVENTION AND TREATMENT OF DIABETIC KIDNEY DISEASE

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCES CITED

U.S. Patent Documents

U.S. Pat. No. 3,175,943 (March 1965. Molho D. et. al.)
U.S. Pat. No. 4,241,047 (December 1980. Lechevin J-C et al.)
U.S. Pat. No. 6,407,073 (June 2002. Trkovnik M et al.)
US Pat. Appl. 20040023893 (February, 2004. Prosdocimi, M, et al.)
U.S. Pat. No. 9,387,245 (July 2016. Johnson R. J. et al.)
US Pat. Appl. 20180201640 (July, 2018. Nagy; N, et al.).
U.S. Pat. No. 10,285,976 (May, 2019. Bollyky P. L. et al.)

BRIEF SUMMARY OF THE INVENTION

The present invention relates to a method for preventing Diabetic Kidney Disease (DKD) or delaying its progression to End-Stage-Renal-Disease. In particular, the inventors have found that it is possible to effectively treat DKD by inhibiting the synthesis of hyaluronan in a patient in need thereof through the administration of a composition containing a therapeutically effective amount of at least one active agent that reduces the production of hyaluronans such as 4-Methylumbelliferone.

BACKGROUND OF THE INVENTION

Approximately 30% of patients with diabetes develop diabetic nephropathy (DN) (Lai K N, Tang S C W (eds). Contrib Nephrol. Karger, Basel. 2011, vol. 170). Diabetic nephropathy is characterized by diffuse or nodular glomerulosclerosis, afferent and efferent hyaline arteriolosclerosis, and tubulointerstitial fibrosis and atrophy. DN is the single most common cause of end-stage renal failure in the United States and worldwide, as well as the leading reason for dialysis and transplantation (Estacio R. O., Schrier R. W. Adv Int Med 2001. Vol. 46, p 359-408).

Improvements in the management of hyperglycemia and hypertension have reduced the proportion of patients with diabetes reaching end-stage renal disease (Finne P., et al. JAMA. 2005, vol. 294(14), p. 1782-1787); however, additional therapies are required to target those at risk or with progressive diabetic nephropathies. Unfortunately, the results of clinical trials in DN have been largely disappointing for years (Parving H. H., et al. New Eng J Med. 2012, vol. 367(23), p. 2204-2213; de Zeeuw D., et al. New Eng J Med. 2013, vol. 369(26), p. 2492-2503; Fried L. F., et al. New Eng J Med. 2013, vol. 369(20), p. 1892-1903; Fernandez-Fernandez B., et al. Nat Rev Nephrol. 2014, vol. 10(6), p. 325-346). In fact, there is only one therapy just approved by the FDA after canagliflozin recently showed vascular and renal protective effects in diabetic patients (Perkovic V., et al. N Engl J Med. 2019; vol. 380(24), p. 2295-2306; https://www.healio.com/endocrinology/diabetes/news/online/%7Bcc8ba13e-56f7-45f7-87f8-1851895d4ce5%7D/fda-approves-canagliflozin-to-treat-diabetic-kidney-disease-heart-failure-hospitalization?utm_source=selligent&utm_medium=email&utm_campaign=endocrinology%20news&m_bt=174131724805).

The pathophysiological mechanisms that eventually lead to nephropathy and the morphological features of diabetic renal lesions are similar in type 1 and type 2 diabetes mellitus (Parving H. H. Kidney Int. 2001. Vol. 60, p. 2041-55). Various factors are involved in the pathogenesis of diabetic nephropathy including genetic susceptibility to develop nephropathy (Berger M., et al. Kidney Blood Press Res 2003, vol. 26, p 143-54), and hemodynamic factors that cause glomerular hyperfiltration and biochemical changes (Helal I., et al. Nature Reviews Nephrology. 2012. Vol. 8, p 293-300; Reidy K., et al. J Clin Invest. 2014. vol. 124(6), p. 2333-2340).

Hyalinization is an important morphological feature distinguishing diabetic nephropathy from hypertensive nephropathy (Alsaad K. O. and Herzenberg A. M. J Clin Pathol. 2007. vol 60, p 18-26).

Hyaluronan (HA) is a nonsulfated linear glycosaminoglycan that is composed of repeating units of D-glucuronic acid (GlcUA) and N-acetylglucosamine (G1cNAc) (Necas J., et al. Veterinarni Medicina. 2008, vol. 53(8), p. 397-411). It is produced at the plasma membrane by HA synthases, which use cytosolic UDP-GlcUA and UDP-GlcNAc as substrates (Vigetti D., et al. Biochimica et Biophysica Acta—General Subjects. 2014, vol. 1840(8), p. 2452-2459).

Because of the physicochemical properties of hyaluronan solutions, various physiological functions have been assigned to it, including lubrication, water homeostasis, filtering effects, and regulation of plasma protein distribution (Fraser J. R. E., et al. Journal of Internal Medicine. 1997, vol. 242, p. 27-33). HA is recognized as an important structural component of the extracellular matrix, but it also interacts with cells during embryonic development, wound healing, inflammation, and cancer; i.e., important features in normal and pathological conditions (Jiang D., et al. Physiological Reviews. 2011. vol. 91(1), p. 221-264; Contreras E. G., et al. Development. 2009, vol. 136, p. 2987-2996; Litwiniuk M., et al. Wounds. 2016, vol. 28(3), p. 78-88; Hyaluronan in Cancer Biology. Edited by Robert Stern. 2009, Elsevier Inc. ISBN: 978-0-12-374178-3).

It has been proposed that high molecular weight HA typically have anti-inflammatory and antiangiogenic properties and inhibit cell proliferation; while, low molecular weight HA show opposite characteristics, favoring inflammation and promoting cell growth (Stern R., et al. European Journal of Cell Biology. 2006. vol. 85(8), p. 699-715; Cuixia Yang, et al. J Biol Chem. 2012, vol. 287(51), p. 43094-43107).

HA is found in most parts of the human body but in higher concentrations in soft connective tissues (Fraser J. R. E., et al. Journal of Internal Medicine. 1997, vol. 242, p. 27-33). In the kidney, it is primarily found in the interstitial spaces of the medulla (Hansell P., et al. Kidney Int. 2000, vol. 58, p. 2061-2068; Wells A. F., et al. Transplantation. 1990. vol. 50, p. 240-243), where it participates in fluid balance regulation because of its highly hygroscopic properties (Stridh S., et al. Am J Physiol Regul Integr Comp Physiol. 2012. vol. 302: R1235-R1249).

One major producer of HA in the kidney is the renomedullary interstitial cell, which expresses receptors, growth factors, and hormones involved in kidney physiology and pathology (Goransson V., et al. Matrix Biol. 2001, vol. 20, p. 129-136). HA is also synthesized and secreted from the apical membrane of tubular cells when they regenerate because of inflammation (Asselman M., et al. Kidney Int. 2005, vol. 68, p. 71-83), or during hyperglycemic conditions (Jones S., et al. Kidney Int. 2001, vol. 59, p. 1739-1'749). Mesangial cells and vascular smooth muscle cells are also capable of forming HA, which is induced by hyperglycemia (Erikstrup C., et al. Eur J Endocrinol. 2001, vol. 145, p. 193-198; Wang A. and Hascall V. C. J Biol Chem. 2004, vol. 279, p. 10279-10285).

HA and diabetes may be linked because of the close connection between glucose metabolism and HA synthesis. In fact, HA amounts and HA staining in vessels are known to be elevated in serum of diabetic patients (Heickendorff L., et al. Diabetologia. 1994, vol. 37(3), p. 286-292; Morita M., et al. Biomarkers. 2014, vol. 19(6), p. 493-497). Similar results were found in a porcine model of diabetes and in SMCs grown in diabetes mimicking medium (McDonald T. O., et al. Journal of Histochemistry and Cytochemistry. 2007, vol. 55(11), p. 1149-1157; Sainio A., et al. Glycobiology. 2010, vol. 20(9), p. 1117-1126). Moreover, rat mesangial cells increase HA production in hyperglycemic conditions and recruit immune cells in a HA-dependent manner (Wang A. and Hascall V. C. J Biol Chem. 2004, vol. 279, p. 10279-10285; Lewis A., et al. Histology and Histopathology. 2008, vol. 23(6), p. 731-739; Wang A., et al. FEBS Journal. 2011, vol. 278(9), p. 1412-1418).

HA could play an important role in the pathogenesis of type 1 diabetes mellitus. It has been shown that HA is linked to the inflammation of pancreatic islets (Bogdani M., et al. Diabetes. 2014, vol. 63(8), p. 2727-2743). More recently, it was demonstrated that HA is present during the pathogenesis of autoimmune diabetes, and its deposits are temporally and anatomically associated with the development of insulitis; furthermore, a treatment with an inhibitor of HA synthesis, 4-Methylumbelliferone, halted progression to type 1 diabetes even after the onset of autoimmune insulitis in two mice models (Nagy N., et al. J. Clin. Invest. 2015, vol. 125(10), p. 3928-3940).

Hyaluronans have been found related to inflammatory or immunological disorders through their relationship with the production of inflammatory cytokines and growth factors, and most of the research to inhibit their synthesis for targeting a disease has been focused on cancer and immunological disorders (reviewed in: Karbownik M. S., and Nowak J. Z. Pharmacol Rep. 2013, vol. 65(5), p. 1056-1074; Nagy N., et al. Frontiers in Immunology. 2015, vol. 6. doi:10.3389/fimmu.2015.00123).

Overall, not much attention has been paid to the effects of hyaluronan accumulation on organ functioning and health because of hyaluronan accumulation is mainly seen as a result of the disease and not as a cause or main contributor to its aggravation.

Increased hyaluronan production and accumulation in kidneys is a distinctive trait of diabetic nephropathies. However, the role of hyaluronan in the development and progression of Diabetic Kidney Disease remains obscure, and most research efforts have been focused on the mechanisms, proinflammatory cytokines, and transcription factors involved in the induction of Hyaluronan synthases and not on the effects of hyaluronan accumulation on the organ or on the progression of the disease (Reidy K., et al. J Clin Invest. 2014. vol. 124(6), p. 2333-2340; Vigetti D., et al. Biochimica et Biophysica Acta—General Subjects. 2014, vol. 1840(8), p. 2452-2459; Stridh S., et al. Am J Physiol Regul Integr Comp Physiol. 2012. vol. 302: R1235-R1249; Moretto P., et al. Journal of Diabetes Research. Hindawi Publishing Corporation. Volume 2015, doi:10.1155/2015/167283).

Lewis et al. (Lewis A., et al. Histology and Histopathology. 2008, vol. 23(6), p. 731-739) note the unclear role of HA in nephropathies while commenting that "HA may have either disease promoting activity or potentially beneficial disease-limiting effects"; and they remark that their results suggest that "interstitial HA is not involved in inflammatory cell recruitment and is unlikely that it plays a direct role promoting the fibrotic response" in kidneys. Further, these authors showed that increased hyaluronans levels in the kidney are not predictive of diabetic kidney disease progression, additionally obfuscating the role of hyaluronans in diabetic kidney disease.

Thus, while some authors suggest that HA may be involved in the pathogenesis of diabetic nephropathy based on the facts that HA accumulates in kidneys during DKD, and that several kidney cells produce HA at an increased rate during in vitro culture under hyperglycemia (Jones S, et al. Kidney Int 59: 1739-1749, 2001; Mahadevan P, et al. Diabetologia 38: 298-305, 1995; Takeda M, et al. Metab Clin Exp 50: 789-794, 2001; Wang A. and Hascall V. C. J Biol Chem. 2004, vol. 279, p. 10279-10285); others scientists, postulate that HA could have protective beneficial and anti-inflammatory effects in the diabetic kidney (Campo G M, et al. Biochim Biophys Acta 1802: 1118-1130, 2010; Selbi W. D., et al. J. Am. Soc. Nephrol. 2004, vol. 15, p. 1199-1211; Zhang X. L., et al. J. Pathol. 2004, vol. 165, p. 763-T73; Ito T., et al. Am. J. Pathol. 2004, vol. 164, 1979-1988; Ito T., et al. J. Biol. Chem. 2004, vol. 279, p. 25326-25332). Then, it is possible a connection between hyaluronan synthesis and diabetic nephropathy, but the precise mechanisms and consequences of HA involvement in this pathology are still to be clarified. As a matter of fact, considering the filtering properties and important role of HA in water homeostasis, its accumulation in kidneys during diabetes could be understood as a compensatory and/or protecting mechanism given the deterioration of the renal functions.

From above state-of-the-art remarks, it is clear that our idea on inhibiting hyaluronan synthesis for preventing or delaying the progression of diabetic nephropathy is not obvious based on the up-to-date knowledge. This situation is supported by the fact that so far no one has advanced or explored our embodiment to treat DKD despite the unmet need of treatments to target this widespread life-threatening condition.

HA synthesis can be selectively inhibited by 4-Methylumbelliferone (4-MU), a 7-hydroxy-4-methylcoumarin derivative, because of glucuronidation of 4-MU by endogenous UDP-glucuronyltransferases results in a cytosolic depletion of UDP-GlcUA (Nakamura T., et al. Biochem Biophys Res Commun. 1995, vol. 208, p. 470-475; Kakizaki I., et al. J. Biol. Chem. 2004, vol. 279 (32), p. 33281-33289). Moreover, 4-MU can also hinder the hyaluronan synthesis activity by downregulating the expression of hyaluronan synthases (Kultti A, et al. Exp Cell Res. 2009, vol. 315(11), p. 1914-1923).

4-MU (Hymecromone, Heparvit) has been clinically tested for disorders of the bile ducts for several years (Quaranta S., et al. Clin Ter. 1984, vol. 108(6), p. 513-517; Abate A., et al. Drugs Exp Clin Res. 2001, vol. 27(5-6), p. 223-231). 4-MU is a dietary supplement sold OTC as choleretic and antispasmodic drug in Europe and Asia. 4-MU can be administered orally, has low toxicity, and is cheap to produce (Karbownik M. S., et al. Pharmacol Rep.

2013, vol. 65(5), p. 1056-1074). 4-MU is rapidly metabolized in vivo to form 4-Methulumbelliferone glucuronide (4-MUG) and 4-Methylumbelliferone sulphate (4-MUS) (Kuipers H F, et. al. Clin Exp Immunol. 2016, vol. 185(3), p. 372-381). 4-MU metabolites have also HA inhibitory activity, a longer half-life in vivo, and they can increase 4-MU bioavailability (Nagy N, et al. J Biol Chem. 2019, vol. 294(19), p. 7864-78T7).

Recently, in vitro and in vivo studies have demonstrated that 4-MU can suppress LPS-Induced Lung Inflammation in mice (McKallip R. J., et al. Inflammation. 2015, vol. 38(3), p. 1250-1259). Moreover, 4-MU has been proposed as a promising therapeutic agent considering the role of HA in the extracellular matrix and its link to inflammatory, allergic/immunological, and malignant disorders (reviewed in Nagy N., et al. Frontiers in Immunology. 2015, vol. 6. doi: 10.3389/fimmu.2015.00123). In fact, several studies have shown that 4-MU is useful as cytostatic or in preventing metastasis of malignant tumor cells in vitro and in animal models of liver, breast, prostate, pancreatic, and renal carcinomas (Yoshihara S., et al. FEBS Lett. 2005, vol. 579 (12), p. 2722-2726; Urakawa H., et al. Int J Cancer. 2012, vol. 130(2), p. 454-466; Yates T. J., et al. J Natl Cancer Inst. 2015, vol. 107(7), doi:10.1093/jnci/djv085; Yoshida E., et al. Oncology Letters. 2016, vol. 12, p. 2337-2344; Benitez A., et al. The Journal of Urology. 2013, vol. 190, p. 285-290).

As in any chronic illness, inflammatory and immune responses are present during the development of Diabetic Kidney Disease. However, anti-inflammatory or immune modulation treatments have proven not useful to prevent or control DKD progression. Moreover, our experimental data suggest that the anti-inflammatory or immune modulation properties of hyaluronan synthesis inhibitors such as 4-Methylumbelliferone, play little or no role in the beneficial effects that we have observed on Diabetic Kidney Disease. Thus, we are dealing with a different mechanism of 4-MU action and the uses of 4-MU described in the state of the art to treat gallbladder, cancer, allergic, or autoimmune disorders do not represent in any way an anticipation or interference to our present patent claim about treating Diabetic Kidney Disease with inhibitors of HA synthesis.

Moretto et al. (Moretto P., et al. Journal of Diabetes Research. Hindawi Publishing Corporation. Volume 2015, doi:10.1155/2015/167283), when discussing the role of hyaluronan in Vascular diseases and Diabetes, point out that critical pro-atherosclerotic properties of HA are demonstrated by using 4-MU as inhibitor of hyaluronan synthesis, and that inhibition of HA synthesis reduces neointima formation in vessels. Moreover, they remark that, 4-MU blocked aortic smooth muscle cell (aSMC) proliferation, migration, and induced apoptosis in vitro. These authors also highlight that high molecular weight hyaluronans can restore cell viability by inhibiting cell death in aSMCs, and that mice lacking the HA cell receptor CD44 are protected against atherosclerosis. However, Moretto et al. do not advance the usefulness of using 4-MU to block hyaluronan synthesis in kidney disease when discussing the role of hyaluronan in diabetes. Neither they anticipate a claim directed to treating diabetic kidney disease through the inhibition of hyaluronan synthesis. Moreover, Moretto et al. only mention the word "kidney" in one paragraph about Epigenetics and Metabolic memory theory, and besides this, they only make general remarks about that "it is possible that HA and diabetes are linked" or that "nephropathies are associated with diabetes". Clearly, the pathophysiology of vascular and kidney diseases are very different, and it is not obvious at all that a treatment designed for the first will be effective for the second. Then, knowing that association does not imply causation, Moretto's et. al. disclosures are irrelevant to our invention based on the state-of-the-art facts described herein.

Colombaro and co-authors (Colombaro V, et al. Nephrol Dial Transplant. 2013, vol. 28(10), p. 2484-93) have shown that 4-MU treatment can reduce hyaluronan content in kidneys and that this inhibition pre and post-operatively is protective against renal ischemia-reperfusion injury (IRI) after kidney transplants. Moreover, the authors show that the mechanism behind this protective effect is based upon the inhibition of the pro-inflammatory responses triggered by the HA-CD44 interaction. However, the pathophysiological process of IRI is unconnected to diabetic kidney disease progression, and the role of inflammatory responses as the main causative agent in the development of Diabetic Kidney Disease remains to be proved. Therefore, Colombaro's et al. disclosure does not anticipate the embodiment of the present invention.

It has been also advanced that blocking the interaction between HA and CD44 cell receptor may preserve the capillary network in chronic renal disease by preventing the development of inflammatory fibrosis mediated by TGF-beta1 (Rouschop K M, et al. J Am Soc Nephrol. 2006, vol. 17(3), p. 746-53). However, the modulation of CD44 receptor activity to change TGF-beta depending inflammatory fibrosis is unrelated to our patent application and it neither makes obvious the object of our invention based on the above-mentioned facts.

Finally, the blockage of overexpressed levels of hyaluronan in kidneys by using hyaluronidases has been proposed as a better alternative to diuretics in nephropathies (Stridh S., Palm F., Hansell P. Am J Physiol Regul Integr Comp Physiol. 2012. vol. 302: R1235-R1249), but it is known that diuretics cannot prevent or delay the progression of Diabetic Kidney Disease and therefore this prior art does not anticipate our idea of inhibiting hyaluronan synthesis to alter the development of DKD.

The most relevant patents or patent applications linking a pharmacological activity of a HA synthesis inhibitors such as 4-Methylumbelliferone and a disease are: U.S. Pat. Nos. 3,175,943; 4,241,047; US Pat. Appl. 20040023893, U.S. Pat. Nos. 6,407,073, 10,285,976; 9,387,245, and US Pat. Appl. 20180201640.

Molho D. et. al. (U.S. Pat. No. 3,175,943) and Lechevin J-C et al. (U.S. Pat. No. 4,241,047) claim the use of 4-MU for its choleretic and biliary lithiasis properties respectively, but these conditions are unrelated to DKD or to HA accumulation, and they did not anticipate in any way the embodiment of our invention.

Prosdocimi M. et al. (US Pat. Appl. 20040023893) claim the use of 4-MU and other coumarin derivatives for the treatment of diverse conditions such as vascular, dermatological, allergic pathologies, hypercholesterolemia, and systemic infections, but not for nephropathies or Diabetic Kidney Disease. Moreover, there are no examples illustrating any pharmacological activity of the prepared chemicals in this application. On the other hand, U.S. Pat. No. 6,407,073 (Trkovnik M et al. June 2002) claims the use of coumarin derivatives for the treatment of digestive tract disorders, and in a general statement they say: "The present invention relates to coumarin derivatives, particularly hymecromone, to pharmaceutical compositions containing them and to their use in the treatment of disorders of the liver, kidney, pancreas, bladder and gastro-intestinal tract"; however, the authors don't show any example of realization applied to kidneys, neither claim any application to treat kidney disorders.

Bollyky P. L. et al. (U.S. Pat. No. 10,285,976) claim the use of anti-inflammatory immuno-modulating properties of 4-MU to treat autoimmune, allergic, or atopic diseases. As we stated before, Diabetic Kidney Disease is not an immunological disease; moreover, the term "nephropathy" is not mentioned in this document, and the word "kidney" is only mentioned once in a broad comment stating that diabetes "can lead to serious problems with the heart, eyes, kidneys, nerves, and gums and teeth". Therefore, this patent does not make obvious, neither preclude, the object of our present invention.

Johnson R. J. et al. (U.S. Pat. No. 9,387,245) claim the use of fructokinase inhibitors to prevent and treat many diseases including "sugar craving, obesity, features of metabolic syndrome (including insulin resistance, hypertriglyceridemia, hypertension, and fatty liver), polyuria, proximal tubular injury, and diabetic kidney disease". Johnson R. J. et al.'s patent is related to fructose metabolism, fat accumulation, and sugar craving; it mentions 4-MU, among a group of dozens of compounds, as an antioxidant that can be used with the patented drug as conjunctive agent, but it is known that antioxidants do not prevent or halt the progression of DKD. This patent has nothing to do with hyaluronan synthesis. As a matter of fact, the term hyaluronan or hyaluronic acid is not mentioned in this document. This patent discloses a different approach using a different target to treat many conditions including DKD. Therefore, this patent does not make obvious, neither preclude, the object of our present invention.

Nagy N. et al. (US Pat. Appl. 20180201640) claim the use of 4-MU derivatives that reduce or prevent HA synthesis to curtail inflammation and treat many immunological and allergic diseases. This patent can be seen as an extension of Bollyky P. L. et al. (U.S. Pat. No. 10,285,976) as the embodiments are based on the same premises. However, Diabetic Kidney Disease is not an immunological disorder per se, and anti-inflammatory therapies have proven to be ineffective to alter the course of the disease. Also, the term "nephropathy" is not mentioned in this patent, and the word "kidney" is only mentioned once in a broad comment stating that diabetes "can lead to serious problems with the heart, eyes, kidneys, nerves, and gums and teeth". Therefore, this patent does not make obvious, neither preclude, the object of our present invention.

Summarizing, the present invention adds a potential new therapy to prevent or halt the progression of Diabetic Kidney Disease to the current limited arsenal of clinical options. Previous studies suggest that inhibitors of HA synthesis such as 4-Methylumbelliferone can target inflammatory and immunological conditions; however, Diabetic Kidney Disease has no immunological origin and anti-inflammatory treatments have provided no relief so far. We have found that inhibitors of HA synthesis can target and modify the progression of DKD by a mechanism probably related to the reduction of HA accumulation that needs to be further investigated and which constitutes the basis for this patent application.

BRIEF DESCRIPTION OF THE DRAWINGS

The following description illustrates the embodiment of this invention which will be better understood when in view of the accompanying drawings, wherein.

DETAILED DESCRIPTION OF THE INVENTION

There is paucity of options to treat Diabetic Kidney Disease in the clinical practice. DKD is the leading cause of ESRD in the US and worldwide. Slowing or preventing DKD will have significant reduction in cost, morbidity, mortality, and associate quality of life. The impact can be significant and large.

The present disclosure describes a new use of HA synthesis inhibitors for the treatment of Diabetic Kidney Disease. To study the effects of HA inhibitors on the development of DKD, our experiments were done by providing the test drug (4-Methylumbelliferone, 4-MU) in the food to one of the best available murine models of diabetic nephropathy, the diabetic and moderately hypertensive endothelial nitric oxide synthase/leptin receptor deficient (eNOS−/−/db/db) mice (Mohan S., et al. Laboratory Investigation. 2008, vol. 88, p. 515-528; Betz B., at al. Nephron Exp Nephrol. 2014, vol. 126, p. 191-195).

At 9 weeks old, the double homozygous mutant eNOS/db mice were separated in two similar groups regarding sex, body weight, non-fasting plasma glucose concentrations, and consanguinity. Experimental animals were fed at libitum identical artificial diets formulated by Envigo-Teklad, containing or not 5% of 4-MU sodium salt (Sigma, cat. no. M1508) until 19 weeks of age. Both diets provided 3.5 Kcal/g and contained by weight: 17.7% of protein, 53.7% of carbohydrate, and 7.2% of fat. Diets were kept sealed under vacuum at −20° C. protected from light. Every week, the old food was removed, and animals were provided fresh food pellets.

Our measures of daily food consumption indicate that treated animals had a dose of 250±50 mg per day of 4-MU (about 5 g/Kg body weight/day). We detected in 4-MU fed animals a reduction of serum hyaluronan content of about 30% after 3 weeks of treatment.

Figure 1:
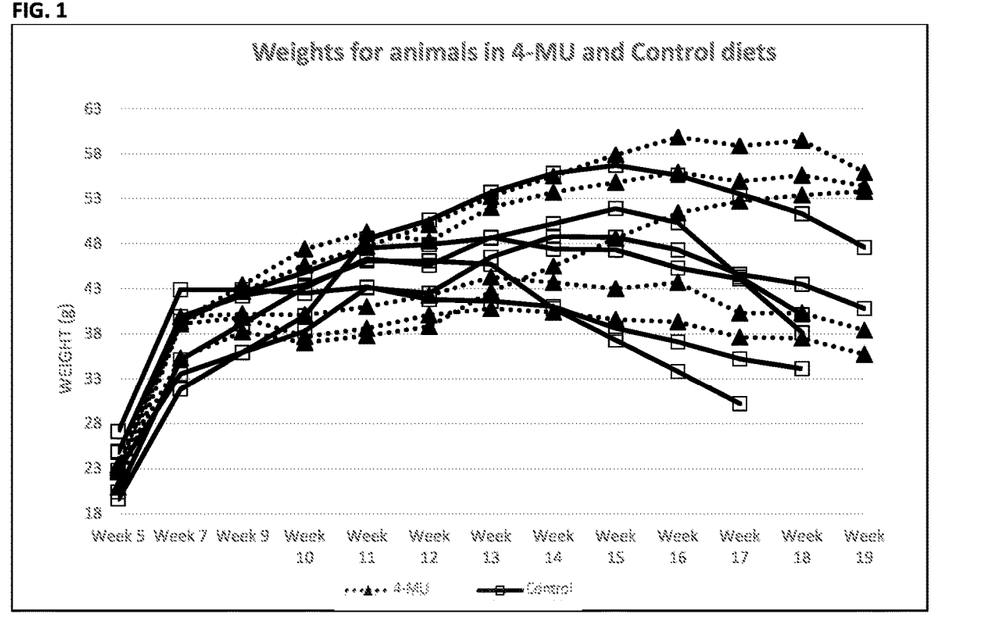
FIG. 1, Body weight changes in 4-MU-treated and untreated (Control) animals by weeks of age. Notice that 4-MU treated animals keep their body weight for a longer period.
Figure 2A:
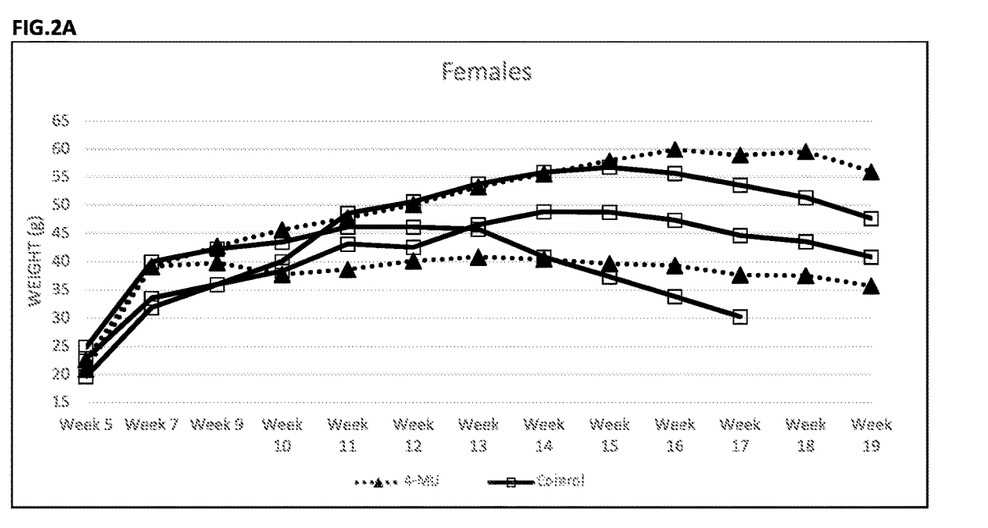
FIG. 2A shows body weight changes in 4-MU-treated and untreated female animals indicating that the observed trend in body weight change is independent of the animal's sex.
Figure 2B:
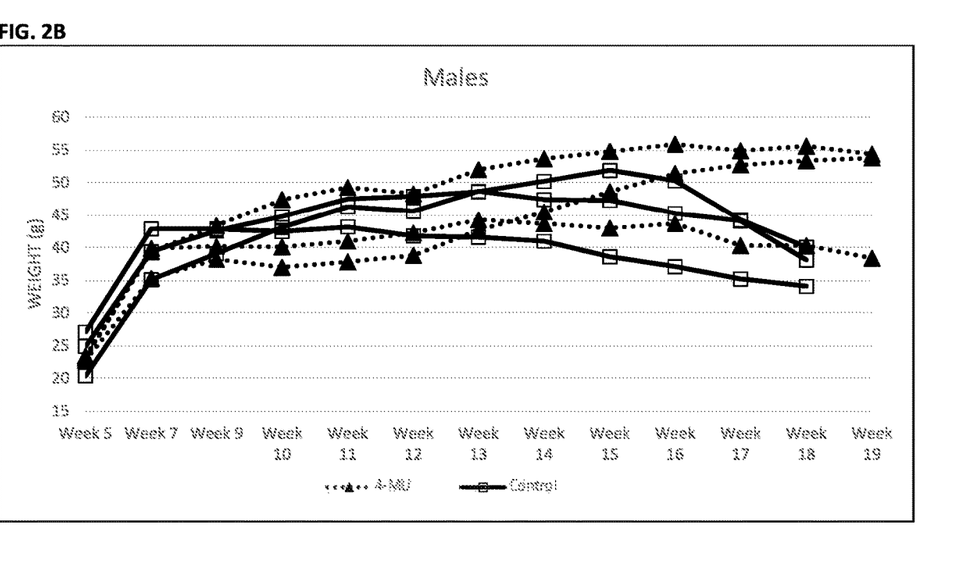
FIG. 2B shows body weight changes in 4-MU-treated and untreated male animals indicating that the observed trend in body weight change is independent of the animal's sex.
Figure 3:
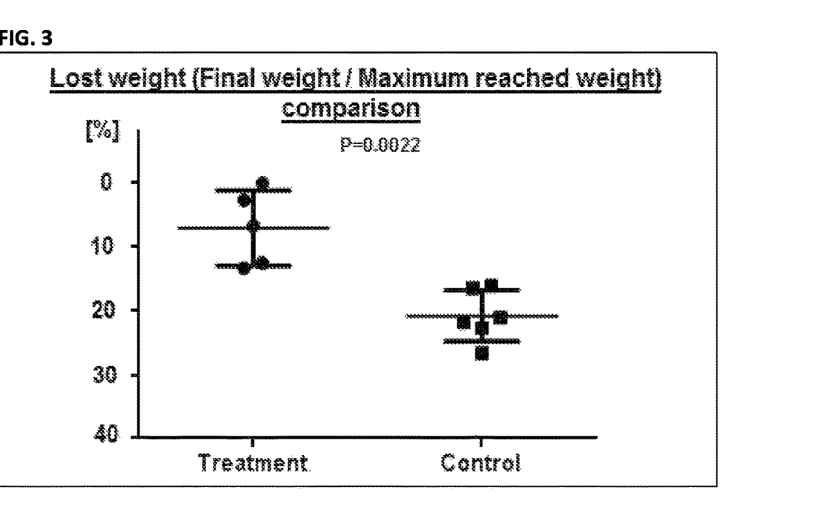
FIG. 3 shows a significant difference in weight loss (final weight divided by maximum reached weight) between 4-MU-treated and untreated (Control) animals at the end of the experiments, indicating that 4-MU treatment positively impact the overall health of these animals.

The weight and appearance of the animals was monitored weekly. We found that mice under 4-MU treatment kept their body weight longer than the mice on control diet at the end of the experimental period (FIG. 1); this finding was independent of the animal's sex (FIG. 2A and FIG. 2B). Of note, at the final stages of the disease, the mice under control diet lost significantly more weight than the mice treated with 4-MU (FIG. 3), highlighting a decline that ended with premature death. Therefore, the administration of 4-MU to DKD animals impacted their overall health and survival.

Figure 4A:
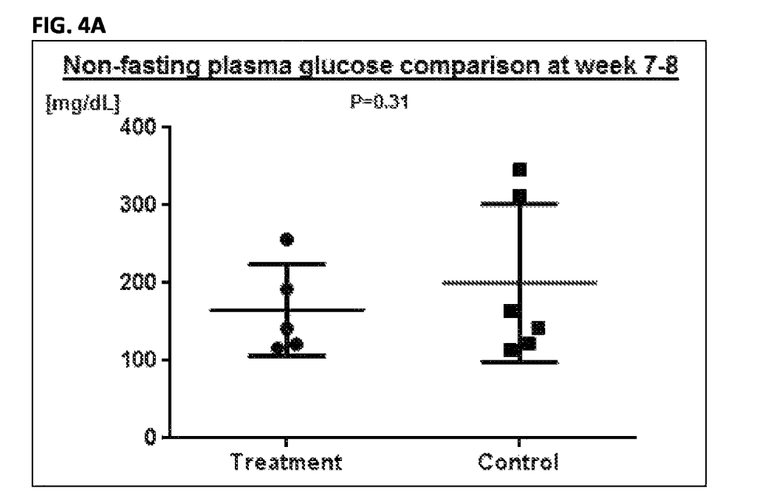
FIG. 4A shows plasma glucose levels in both groups of animals (4-MU treatment and Control) before being fed with the special diets (7-8-week-old). No significant difference in initial plasma glucose levels was found.
Figure 4B:
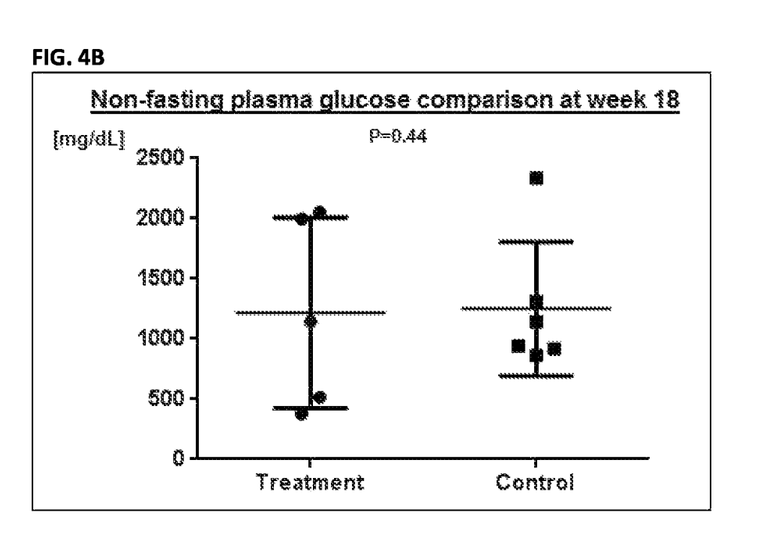
FIG. 4B shows plasma glucose levels in 4-MU-treated and untreated (Control) animals at the end of the experiments after being fed with special diets (18-week-old). No significant difference in final plasma glucose levels was found.

Plasma glucose levels were measured using a commercial kit (EIAGLUC, Invitrogen). In our experiments, 4-MU treatments did not affect non-fasting plasma glucose levels (FIG. 4A and FIG. 4B), indicating that all animals had the same pre-condition to develop the DKD and that 4-MU treatment does not affect the diabetes status in our mice. This fact remarks an important difference between our invention and the use of 4-MU to treat autoimmune diabetes.

Figure 5:
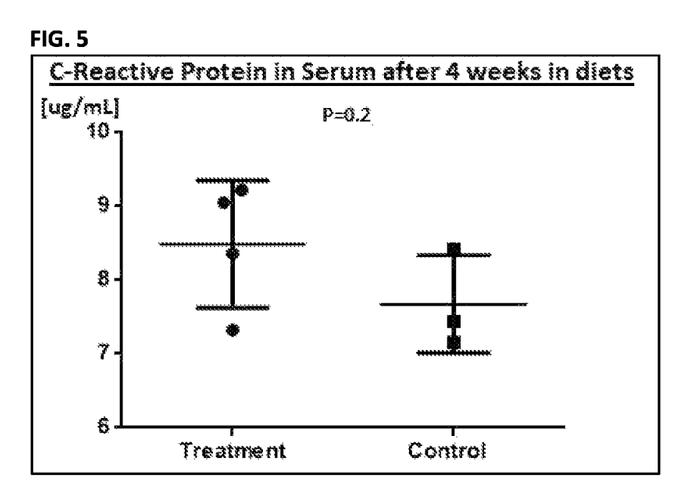
FIG. 5 shows C-Reactive Protein levels in serum of 4-MU-treated and untreated (Control) animals 4 weeks after being fed with the special diets. No significant difference in final serum C-Reactive Protein levels was found.

By using a commercial C-Reactive Protein (C-RP) immunoassay (MCRP00, R&D Systems), we found that there were not significant differences between 4-MU treated and untreated animals regarding the C-RP values in serum (FIG. 5). C—RP is considering the gold standard marker for inflammation and the lack of differences in this protein between our experimental mice points out that 4-MU is not affecting the development of DKD by crucially changing the inflammatory responses in our diabetic animals but for other mechanism of action.

Figure 6A:
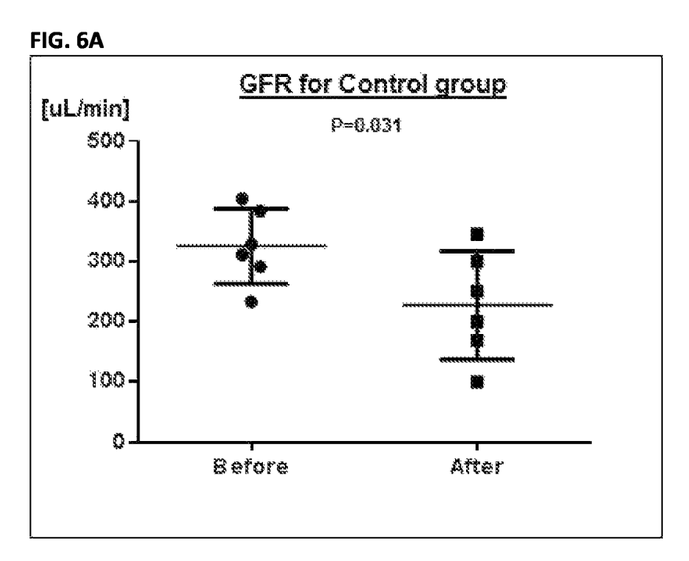
FIG. 6A show Glomerular Filtration rates variations for untreated animals before (week 7-8) and after (week 18) being fed the special Control diet. A significant difference was found between initial and final GFR values for Control animals corresponding with DKD worsening with age.
Figure 6B:
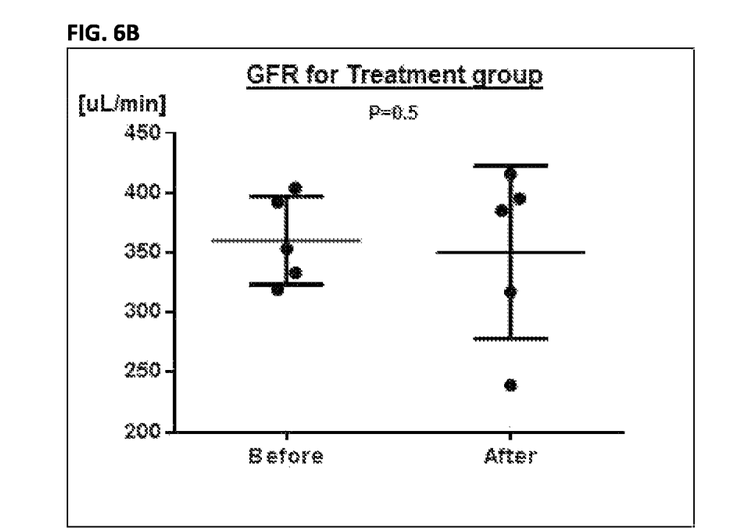
FIG. 6B show Glomerular Filtration rates variations for 4-MU treated animals before (week 7-8) and after (week 18) being fed the special 4-MU diet. No significant difference was found between initial and final GFR values for 4-MU-treated animals.
Figure 6C:
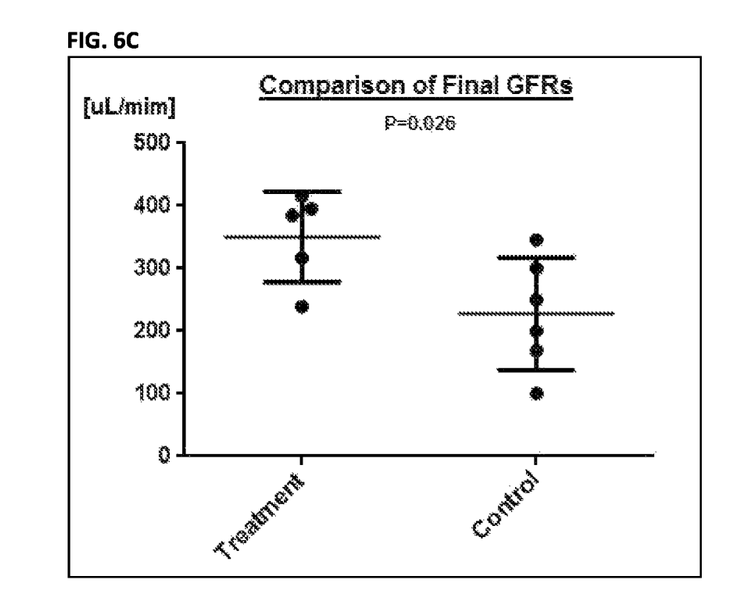
FIG. 6C shows a significant difference between GFRs of 4-MU-treated and Control animals at the end of the experiment after eating special diets for about 10 weeks, illustrating that 4-MU treatment halted the progression of Diabetic Kidney Disease.

Glomerular Filtration Rate (GFR) is the more reliable test to assess kidney function. In our experiments, GFR were determined before (week 8) and after 10 week of treatments (week 18) by a single bolus injection of fluorescein isothiocyanate-(FITC) labeled inulin in conscious mice (Rieg T. J Vis Exp. 2013, May 10: e50330, doi: 10.3791/50330). GFR results indicated that 4-MU treatment significantly delayed the progression of DKD in 4-MU treated mice. A rapid decline in GFR is seen in control animals at the end stages of the DKD right before total kidney failure and death (FIG. 6A). Treated mice kept their GFR values unchanged (FIG. 6B), confirming that 4-MU treatment significantly delayed the progression of DKD (FIG. 6C); that is, our invention works for its intended purpose.

Figure 7A:
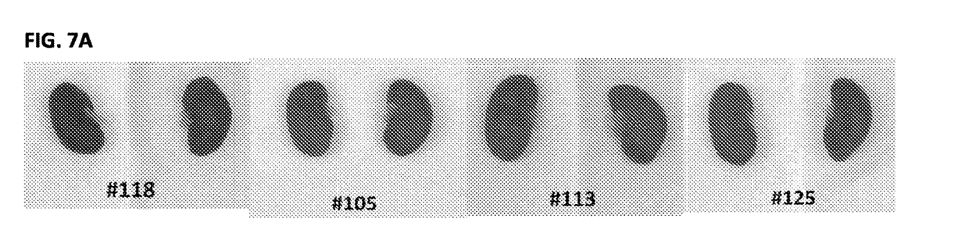
FIG. 7A shows kidney morphology in non-diabetic mice (wild type controls). Photos were taken under the same light conditions and at the same distance. Numbers are animal's tag identifiers.
Figure 7B:
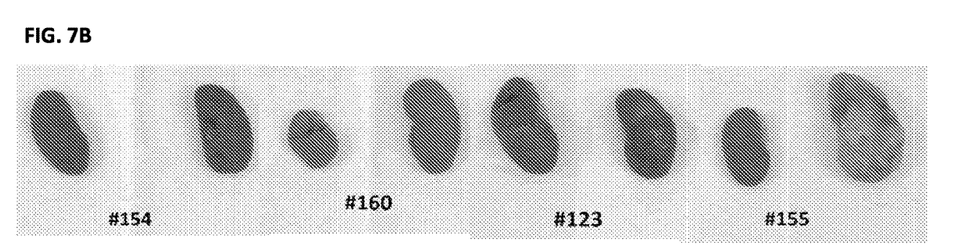
FIG. 7B shows kidney morphology in diabetic mice fed with Control diet. Photos were taken under the same light conditions and at the same distance. When comparing to normal kidneys, notice the atrophied, fibrotic, abnormally gigantic and hyaline kidneys. Numbers are animal's tag identifiers.
Figure 7C:
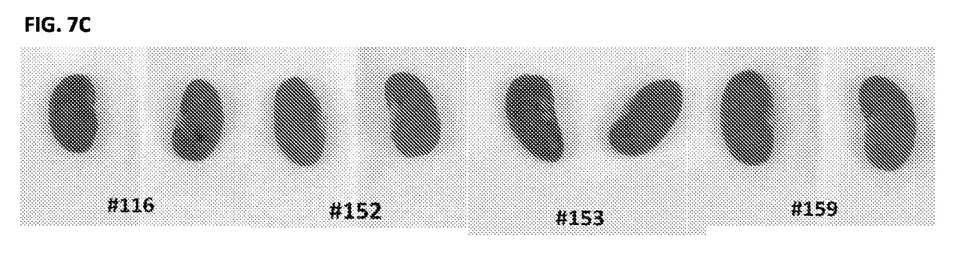
FIG. 7C shows kidney morphology in diabetic mice fed with 4-MU diet. Photos were taken under the same light conditions and at the same distance. When comparing to normal kidneys, notice that abnormalities are less pronounced in this group. Numbers are animal's tag identifiers.

Comparison of kidney morphology also revealed a less advanced degree of DKD in 4-MU treated mice as we found atrophied, or gigantic, abnormal, and fibrotic kidneys only in animals fed with control diet (FIG. 7A, FIG. 7B, FIG. 7C).

Finally, for histopathology analysis kidneys were collected from 4-MU-treated and control mice at the end of the experiment. Organs were fixed in 10% NB formalin for 44 hours, embedded in paraffin, and 3 urn sections were stained with Hematoxylin and Eosin (H&E) or Periodic acid—Schiff (PAS), before being examined following Zhao H J et al. (Zhao H. J., et al. J Am Soc Nephrol. 2006, vol. 17, p. 2664-2669). A semi-quantitative index was used to evaluate the degree of glomerular mesangial expansion and sclerosis. 50 glomeruli on a single section (25 from each kidney) were scored from 0 to 4, where 0 represents no lesions and 1, 2, 3, and 4 represent mesangial matrix expansion or sclerosis involving less than or equal to 25, 26-50, 51-75, or >75% of the glomerular tuft area, respectively. End stage sclerotic glomeruli (glomerulosclerosis) were counted, as well as the number of glomeruli that contained nodules, and the percentage of affected glomeruli within the 50 analyzed. Histopathology staining and analyses were done by an independent service and the specialists were blind regarding the nature of the samples.

Figure 8:
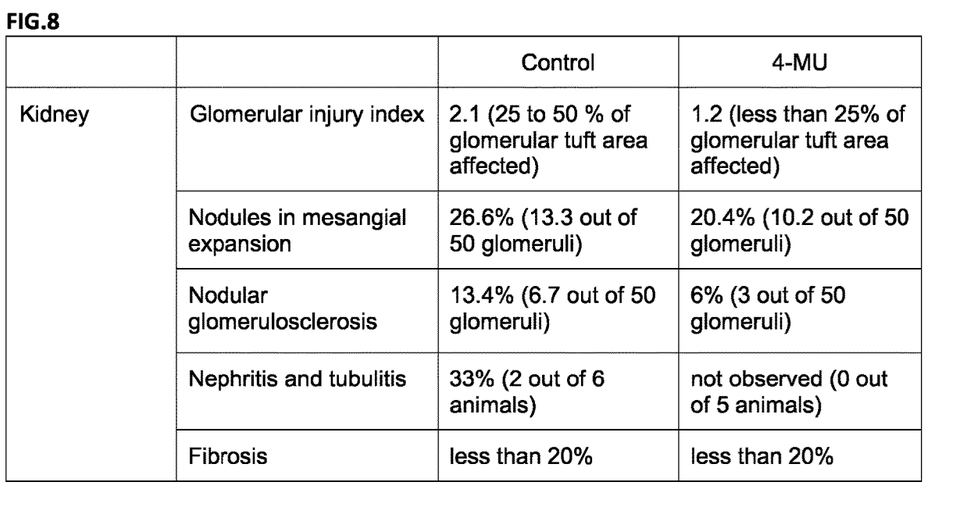
FIG. 8 summarizes the Histopathology results for kidneys, showing that 4-MU-treated mice had a lower degree of kidney injuries.

The histopathology studies confirmed a protective role of 4-MU on diabetic kidney. In 4-MU-treated animals, it was found a significant lower glomerular injury index and lower nodular glomerulosclerosis (FIG. 8). Unlike for control animals, we did not found signs of nephritis and tubulitis in 4-MU-treated mice. However, both groups of animals showed similar degree of fibrosis in kidneys (FIG. 8). This last finding further support our idea about that 4-MU treatment is not strongly modifying the inflammation status in kidneys if considering that fibrotic and inflammatory responses are closely intertwined (Urban M. L., et al. N Engl J Med. 2015, vol. 373(1), p. 95-96; Wynn T. A., et al. Nat Med. 2012, vol. 18(7), p. 1028-1040).

In conclusion, the obtained experimental data fully support our invention regarding the use of 4-Methylumbelliferone as an efficacious treatment for the Diabetic Kidney Disease. We have found that 4-MU can target the development of DKD in a mouse experimental model, revealing that inhibitors of hyaluronan synthesis could be effective drugs for preventing or delaying the progression of diabetic nephropathy. Moreover, considering that we have not detected differences in inflammatory markers (circulating C-RP and degree of fibrosis in kidneys) between the treatment and control groups, we believe that the observed mechanism of 4-MU action on DKD should be mainly through the reduction of HA accumulation and not by altering inflammatory or immune responses as it is the case when using 4-MU to treat cancer and other diseases.

Of note, published results on the use of 4-MU for the treatment of different disorders show that inhibitors of hyaluronan synthesis such as 4-MU can be indistinctly administered orally or parenterally by injections without affecting its biological activity (e.g., Urakawa H., et al. Int J Cancer. 2012, vol. 130(2), p. 454-466; Yates T. J., et al. J Natl Cancer Inst. 2015, vol. 107(7), doi:10.1093/jnci/djv085; Nagy N., et al. J. Clin. Invest. 2015, vol. 125(10), p. 3928-3940).

DKD patients suffer from many comorbidities and usually are under several medications. Therefore, in our method, the active agent will have to be administered while the patient is taking other drugs, or it will have to be co-administered with some of them. Fortunately, there should not be an impediment for this procedure as 4-MU is known to be safe and not prone to provoke significant adverse reactions.

Obviously, the above observed effects of 4-MU on DKD can be also achieved by increasing turnover or eliminating hyaluronans using hyaluronidases, for example. Moreover, it will be clear for anyone skilled in the state of the art that any agent able to halt the synthesis and/or accumulation of hyaluronans in a diabetic patient in need thereof will be suitable for achieving the herein claimed embodiment. Therefore, it will be obvious that the realization example described above is provided only by way of illustration because many substitutions may be made without departing from the embodiment of this invention. Accordingly, this invention will be limited only by the scope of the appended claims.

The terms used in the present disclosure have a clear meaning for one skilled in the art. However, there are a group of terms that require to be defined in order to avoid misunderstanding our claims. As used herein, the term "preventing" means inhibiting the onset of the disease, and the term "delaying the progression" means causing delay in the development of the different diabetic kidney disease stages. The term "active agent" means the compound of the present disclosure that is effective to inhibit the hyaluronan synthesis. The term "composition" means the active agent of the present disclosure, as well as a mix of this agent with pharmaceutically acceptable diluents, carriers, or other medicines when required. The term "therapeutically effective amount" means the amount of the compound of the present disclosure that is effective to achieve the desired therapeutic result, i.e. the inhibition of hyaluronan synthesis and the onset or progression of the disease. The term "derivative" means a compound with pharmacological properties similar to that of the active agent object of the present invention and produced by chemical or enzymatic modifications thereof.

What is claimed is:

1. A method for delaying the progression of Diabetic Kidney Disease through the inhibition of hyaluronan synthesis in a subject in need thereof, wherein said method comprises the administration to said subject of a composition containing a therapeutically effective amount of at least one active agent from the Coumarin group (4-Methylumbelliferone, a 4-Methylumbelliferone metabolite, or a salt thereof) that reduces the amount of hyaluronans in diabetic kidneys.

2. The method of claim 1, wherein the active agent in said composition is administered orally, or parenterally.

* * * * *